United States Patent
Narimatsu (10) Patent No.: US 6,802,814 B2
(45) Date of Patent: Oct. 12, 2004

(54) PRESSURE-PULSE-WAVE DETECTING APPARATUS

(75) Inventor: Kiyoyuki Narimatsu, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 95 days.

(21) Appl. No.: 10/265,399

(22) Filed: Oct. 7, 2002

(65) Prior Publication Data

US 2003/0158489 A1 Aug. 21, 2003

(30) Foreign Application Priority Data

Feb. 18, 2002 (JP) .................................... 2002-039410

(51) Int. Cl.⁷ .............................................. A61B 5/02
(52) U.S. Cl. ..................................... 600/485; 600/500
(58) Field of Search ................................. 600/485–507

(56) References Cited

U.S. PATENT DOCUMENTS 4,653,506 A    3/1987  Romanovskaya
5,238,000 A    8/1993  Niwa
5,261,414 A   11/1993  Aung et al.
6,497,668 B2 * 12/2002  Nishibayashi ............... 600/494
6,610,017 B2 *  8/2003  Oka .......................... 600/485

FOREIGN PATENT DOCUMENTS

EP    1 159 914 A2   12/2001

* cited by examiner

Primary Examiner—Mary Beth Jones
Assistant Examiner—Patricia Mallari
(74) Attorney, Agent, or Firm—Oliff & Berridge, PLC (57) ABSTRACT

An apparatus for detecting a pressure pulse wave from a living subject, including a pressure-pulse-wave sensor which is adapted to be pressed against a portion of the subject to detect the pressure pulse wave from the subject, a pressing device which presses the pressure-pulse-wave sensor against the portion of the subject, a blood-pressure measuring device which measures at least one blood pressure value of the subject, and a comparison-value determining device for determining a comparison value based on the at least one blood pressure value measured by the blood-pressure measuring device and at least one pressure value corresponding to the pressure pulse wave detected by the pressure-pulse-wave sensor.

11 Claims, 7 Drawing Sheets

PRESSURE-PULSE-WAVE DETECTING APPARATUS

BACKGROUND OF THE INVENTION

1. Field of the Invention

The present invention relates to a pressure-pulse-wave detecting apparatus which presses an artery of a living subject and detects a pressure pulse wave produced from the artery.

2. Related Art Statement

There is known a pressure-pulse-wave detecting apparatus which includes a pressure-pulse-wave sensor adapted to be pressed against an artery via skin and detects, through the sensor, a pressure pulse wave produced from the artery. Various sorts of information can be obtained from a shape or form of the thus detected pressure pulse wave. For example, a pulse-wave propagation velocity, i.e., a velocity at which a pulse wave propagates in a living subject may be determined in such a manner that a pressure-pulse-wave sensor is worn on a first portion of the subject to detect a pressure pulse wave from the first portion; a heartbeat-synchronous signal such as a pulse wave or a heart sound is detected from a second portion of the subject; and the pulse-wave propagation velocity is determined based on a time difference between a time of detection of a characteristic point of the pressure pulse wave, such as a rising point or a peak point, and a time of detection of a characteristic point of the heartbeat-synchronous signal. In addition, an augmentation index (hereinafter, referred to as AI) may be determined based on the form of pressure pulse wave. More specifically described, respective peak points of incident-wave and reflected-wave components of a pressure pulse wave are determined; a pressure difference ($\Delta P$) obtained by subtracting a magnitude of the pressure pulse wave at the time of occurrence of the peak point of the incident-wave component, from a magnitude of the pressure pulse wave at the time of occurrence of the peak point of the reflected-wave component, is divided by a pulse pressure, PP, of the pressure pulse wave; and an AI value is determined by multiplying the thus obtained value by 100, according to Expression 1:

$$AI = (\Delta P/PP) \times 100 (\%) \quad \text{(Expression 1)}$$

Measuring an accurate pulse-wave propagation velocity needs to determine an accurate characteristic point of a pressure pulse wave; such as a rising point or a peak point. In addition, determining an accurate AI value needs to determine respective accurate magnitudes of a pressure pulse wave at the respective times of occurrence of respective peak points of incident-wave and reflected-wave components of the pressure pulse wave, and an accurate pulse pressure PP of the pressure pulse wave. That is, obtaining accurate pulse-wave propagation velocity and AI value needs to obtain a pressure pulse wave having an accurate form. If the state in which the pressure-pulse-wave sensor is worn is not appropriate, the pressure pulse wave may be attenuated by the arterial wall and/or the skin or subcutaneous tissue. Therefore, obtaining a pressure pulse wave having an accurate form needs to wear the pressure-pulse-wave sensor in an appropriate manner.

However, the conventional pressure-pulse-wave detecting apparatus cannot judge whether a pressure pulse wave detected by itself has an accurate form, or whether a form of a pressure pulse wave accurately represents change of pressure directly measured in an artery. Thus, it has been difficult for a person such as a doctor or a nurse to judge whether physical information obtained based on the form of pressure pulse wave, such as pulse-wave propagation velocity or AI value, is reliable or not.

SUMMARY OF THE INVENTION

It is therefore an object of the present invention to provide a pressure-pulse-wave detecting apparatus which can judge whether a form of a pressure pulse wave detected by itself is accurate.

The above object has been achieved by the present invention. According to the present invention, there is provided an apparatus for detecting a pressure pulse wave from a living subject, comprising a pressure-pulse-wave sensor which is adapted to be pressed against a portion of the subject to detect the pressure pulse wave from the subject; a pressing device which presses the pressure-pulse-wave sensor against the portion of the subject; a blood-pressure measuring device which measures at least one blood pressure value of the subject; and a comparison-value determining means for determining a comparison value based on said at least one blood pressure value measured by the blood-pressure measuring device and at least one pressure value corresponding to the pressure pulse wave detected by the pressure-pulse-wave sensor.

The blood-pressure value or values measured by the blood-pressure measuring device can be deemed as accurate intraarterial pressure values. Therefore, if the comparison value determined by the comparison-value determining means indicates that the pressure value corresponding to the pressure pulse wave is near to the blood-pressure value, it can be judged that the pressure value corresponding to the pressure pulse wave accurately indicates an intraarterial pressure value. In this case, it can be judged that there is substantially no attenuation of the pressure pulse wave because of the arterial wall and/or the skin or subcutaneous tissue, and that the form of the pressure pulse wave is accurate.

According to a preferred feature of the present invention, the blood-pressure measuring device measures a systolic blood pressure value and a diastolic blood pressure value of the subject, and the comparison-value determining means determines the comparison value based on a difference between the systolic and diastolic blood pressure values measured by the blood-pressure measuring device and a pulse pressure corresponding to the pressure pulse wave detected by the pressure-pulse-wave sensor.

A pulse pressure is a difference between the highest pressure corresponding to the greatest magnitude of one heartbeat-synchronous pulse of the pressure pulse wave, and the lowest pressure corresponding to the smallest magnitude of the same pulse. The systolic and diastolic blood-pressure values are the highest and lowest intraarterial pressure values, respectively. Thus, the comparison value is determined based on the difference between the highest and lowest pressure values corresponding to the pressure pulse wave, and the difference between the highest and lowest intraarterial pressure values. Therefore, if the comparison value indicates that the pulse pressure is near to the blood-pressure difference, then it can be judged that there is substantially no attenuation of the pressure pulse wave because of the arterial wall and/or the skin or subcutaneous tissue, and that the form of the pressure pulse wave is accurate.

According to another feature of the present invention, the pressure-pulse-wave detecting apparatus further comprises a judging means for judging, based on the comparison value determined by the comparison-value determining means, whether a state in which the pressure-pulse-wave sensor is worn on the portion of the subject is appropriate.

According to this feature, the apparatus can easily judge whether the state in which the pressure-pulse-wave sensor is worn is appropriate.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
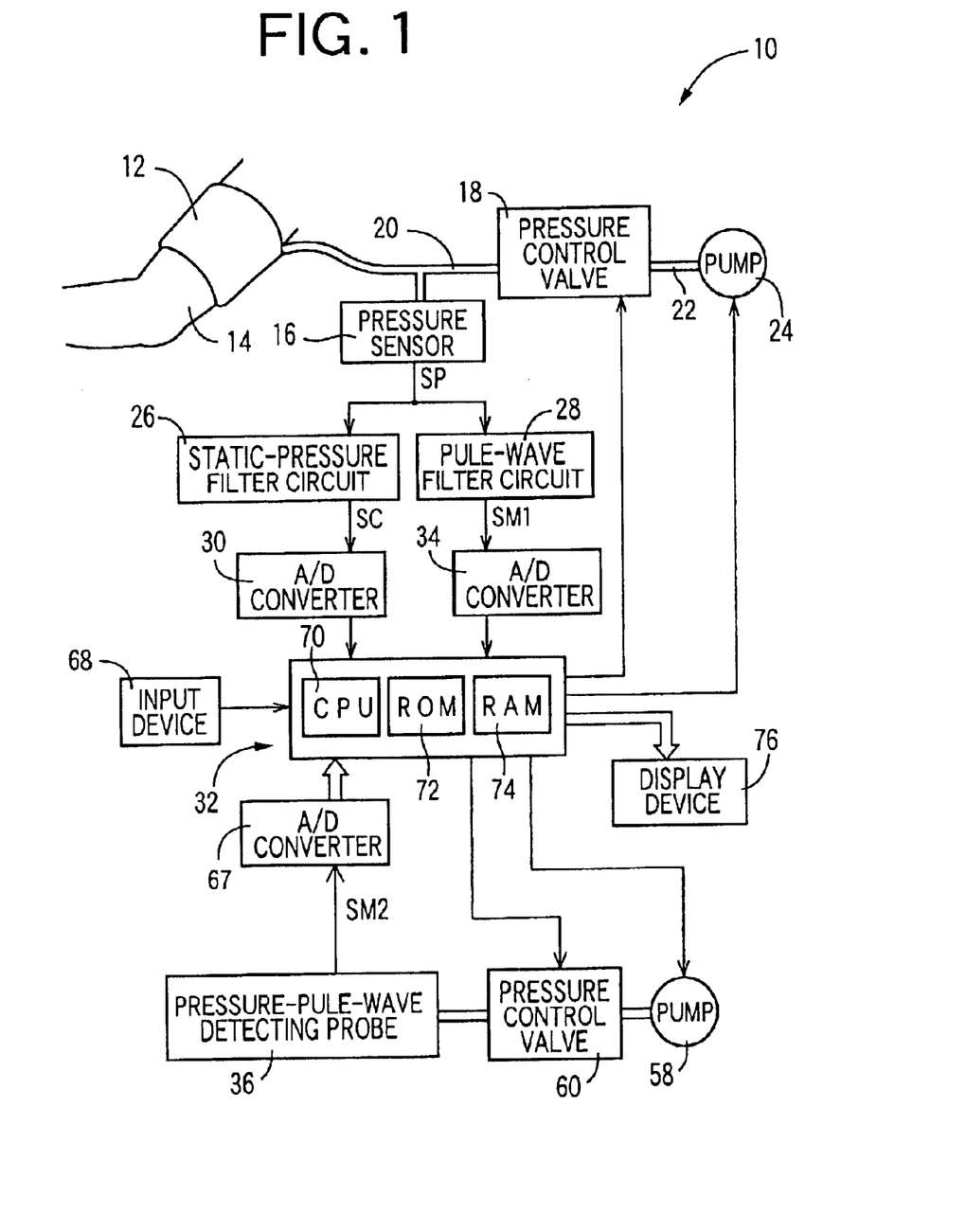
FIG. 1 is a diagrammatic view showing a circuitry of a pressure-pulse-wave detecting apparatus to which the present invention is applied.

Hereinafter, there will be described an embodiment of the present invention in detail by reference to the drawings. FIG. 1 is a diagrammatic view showing a circuitry of a pressure-pulse-wave detecting apparatus 10 to which the present invention is applied.

In FIG. 1, reference numeral 12 designates an inflatable cuff which includes a belt-like cloth bag and a rubber bag accommodated in the cloth bag and which is adapted to be worn on an upper portion 14 of a patient as a living subject. The cuff 12 is connected via a piping 20 to a pressure sensor 16 and a pressure control valve 18. The pressure control valve 18 is connected via a piping 22 to an air pump 24. The pressure control valve 18 adjusts a pressure of a pressurized air supplied from the air pump 24, and supplies the pressure-adjusted air to the cuff 12, or discharges the pressurized air from the cuff 12, so as to control an air pressure in the cuff 12.

The pressure sensor 16 detects the air pressure in the cuff 12, and supplies a pressure signal, SP, representing the detected air pressure, to a static-pressure filter circuit 26 and a pulse-wave filter circuit 28. The static-pressure filter circuit 26 includes a low-pass filter that extracts, from the pressure signal SP, a cuff-pressure signal, SC, representing a static component of the detected air pressure, i.e., a pressing pressure of the cuff 12 (hereinafter, referred to as the cuff pressure, PC). The filter circuit 26 supplies the cuff-pressure signal SC to an electronic control device 32 via an A/D (analog-to-digital) converter 30. The pulse-wave filter circuit 28 includes a band-pass filter that extracts, from the pressure signal SP, a cuff-pulse-wave signal, SM1, representing an oscillatory component of the detected air pressure that has prescribed frequencies. The filter circuit 28 supplies the cuff-pulse-wave signal SM1 to the control device 32 via an A/D converter 34. The oscillatory component represented by the cuff-pulse-wave signal SM1 is a brachial pulse wave that is transmitted to the cuff 12 from a brachial artery, not shown, of the upper arm 14 being pressed by the cuff 12.

Figure 2:
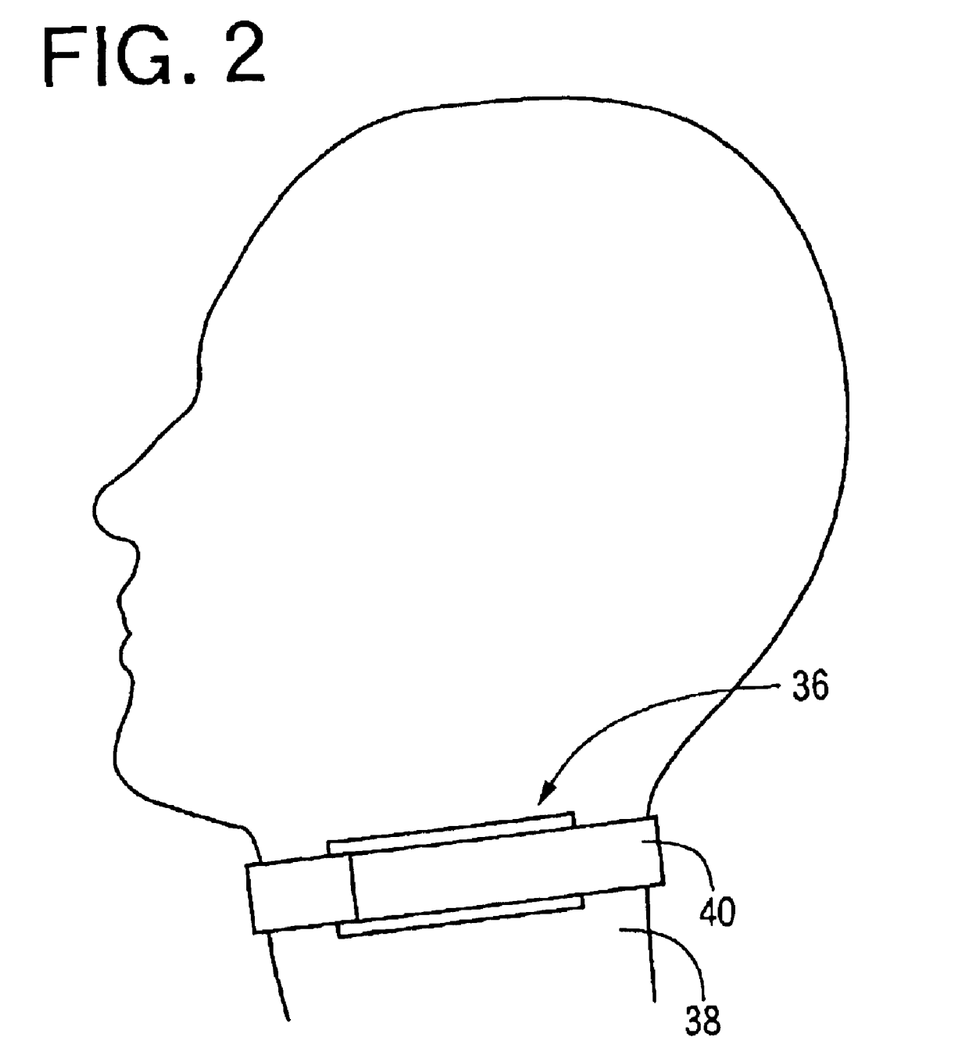
FIG. 2 is an illustrative view showing a state in which a pressure-pulse-wave detecting probe of the apparatus of FIG. 1 is worn on a neck portion of a living subject.

The pressure-pulse-wave detecting apparatus 10 includes a pressure-pulse-wave detecting probe 36 shown in FIG. 2. The pressure-pulse-wave detecting probe 36 is worn on a neck portion 38 of the subject, as illustrated in FIG. 2, with the help of a band 40, so as to non-invasively detect a carotid pulse wave, wc. As shown in detail in FIG. 3, the pressure-pulse-wave detecting probe 36 includes a container-like sensor housing 42; a case 44 which accommodates the sensor housing 42; and a feed screw 48 which is threadedly engaged with the sensor housing 42 and is rotated by an electric motor, not shown, provided in the case 44 so as to move the sensor housing 42 in a widthwise direction of a carotid artery 46. With the help of the band 40, the pressure-pulse-wave detecting probe 36 is detachably attached to the neck portion 38, such that an open end of the sensor housing 42 is opposed to a body surface 50 of the neck portion 38.

Figure 3:
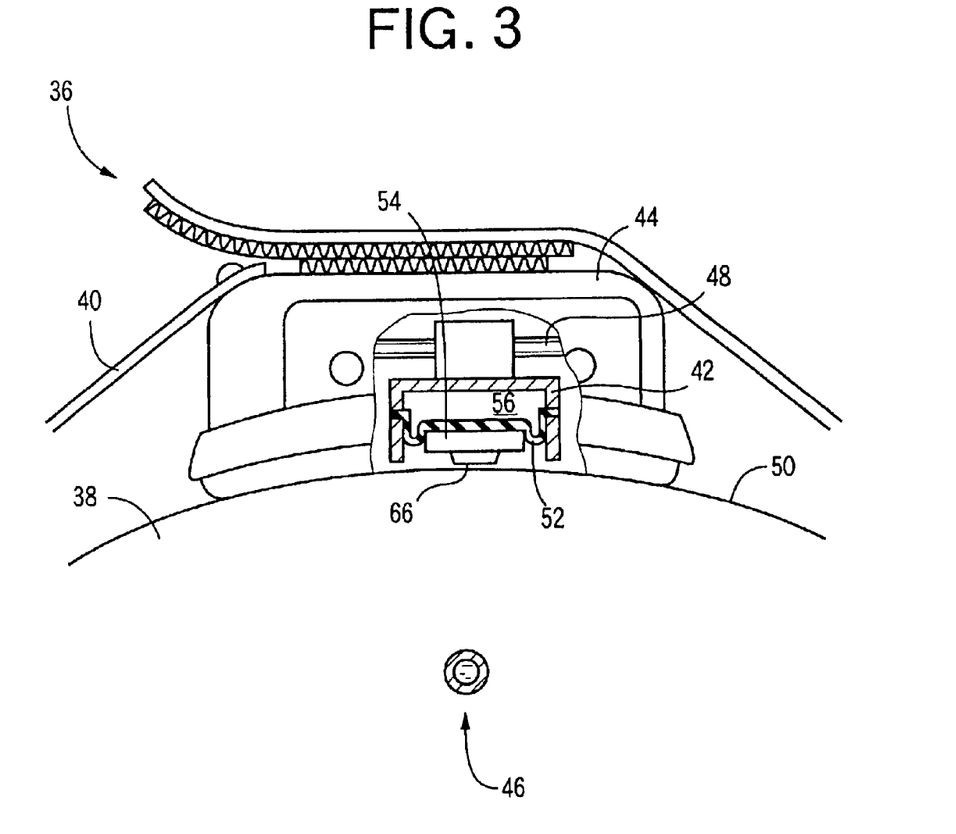
FIG. 3 is an enlarged view of the pressure-pulse-wave detecting probe of FIG. 2, a portion of the probe being cut away.

In addition, the pressure-pulse-wave detecting probe 36 includes a pressure-pulse-wave sensor 54 which is secured via a diaphragm 52 to an inner wall of the sensor housing 42, such that the sensor 54 is movable relative to the housing 42 and is advanceable out of the open end of the same 42. The sensor housing 42, the diaphragm 52, etc. cooperate with one another to define a pressure chamber 56, which is supplied with a pressurized air from an air pump 58 via a pressure-control valve 60, as shown in FIG. 1, so that the pressure-pulse-wave sensor 54 is pressed against the body surface 50 with a pressing force corresponding to the air pressure in the pressure chamber 56.

The sensor housing 42 and the diaphragm 52 cooperate with each other to provide a pressing device 62 which presses the pressure-pulse-wave sensor 54 against the carotid artery 46, and the feed screw 48 and the not-shown motor cooperate with each other to provide a widthwise-direction moving device 64 which moves the pressure-pulse-wave sensor 54 in the widthwise direction of the carotid artery 46 and thereby changes a pressing position where the sensor 54 is pressed on the body surface 50.

Figure 4:
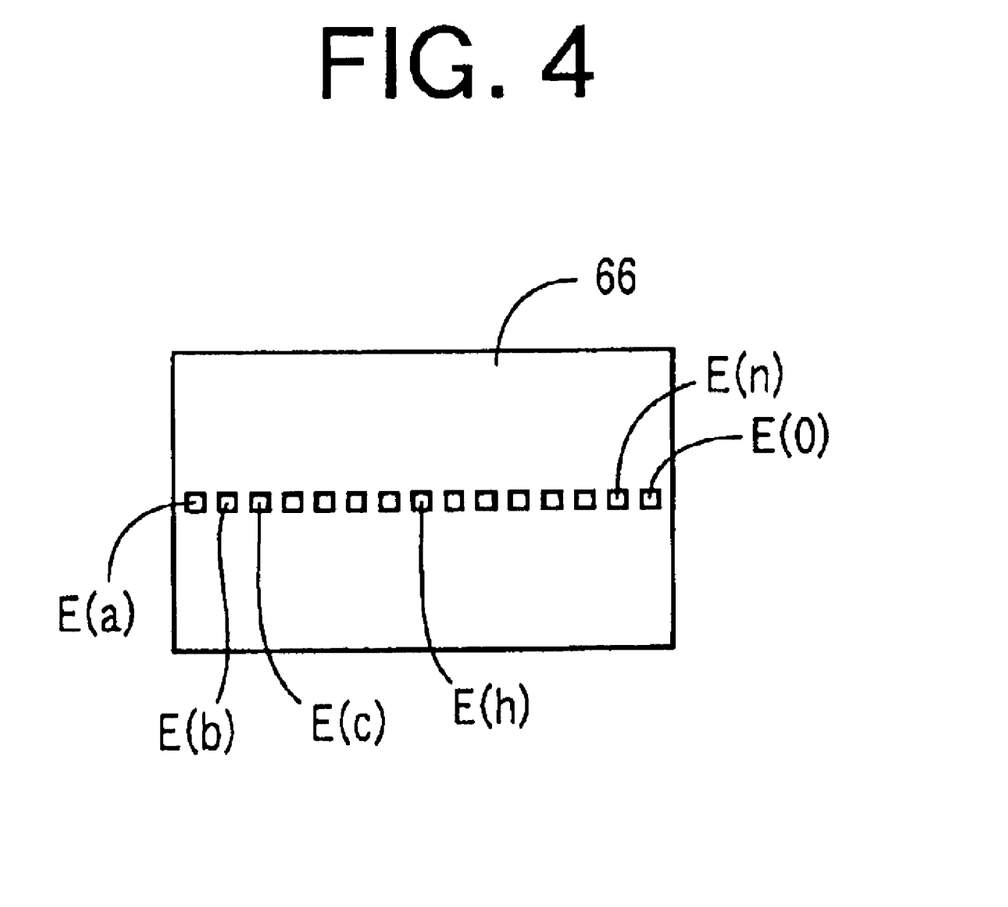
FIG. 4 is a view for explaining a state in which an array of pressure-sensing elements is provided in a press surface of a pressure-pulse-wave sensor shown in FIG. 3.

The pressure-pulse-wave sensor 54 has a pressing surface 66, and a number of semiconductor pressure-sensing elements (hereinafter, referred to as the "pressure-sensing elements") E which are arranged in the pressing surface 66 at a regular interval in the widthwise direction of the carotid artery 46, i.e., in the direction of movement of the sensor 54 parallel to the feed screw 48, over a length greater than the diameter of the carotid artery 46. For example, as shown in FIG. 4, fifteen pressure-sensing elements E(a), E(b), . . . , E(o) are arranged at a regular interval of, e.g., 0.6 mm.

The pressure-pulse-wave detecting probe 36, constructed as described above, is pressed against the body surface 50 of the neck portion 38 right above the carotid artery 46, so that the pressure-pulse-wave sensor 54 detects a pressure pulse wave (i.e., a carotid pulse wave, wc) which is produced from the carotid artery 46 and is propagated to the body surface 50, and supplies a pressure-pulse-wave signal SM2 representing the detected carotid pulse wave wc, to the control device 32 via an A/D converter 68.

An input device 68 includes a plurality of input keys, not shown, which are operated by an operator such as a doctor or a nurse to set a pressing force, HDP, with which the pressing device 62 presses the pressure-pulse-wave sensor 54, and operate the widthwise moving device 64 to move the pressure-pulse-wave sensor 54 and thereby change a pressing position where the pressing device presses the sensor 54. When the input keys are operated, the input device 68 supplies, to the control device 32, a pressing-force signal representing the pre-set pressing force HDP, and a pressing-position changing signal to change the pressing position where the sensor 54 is pressed.

The electronic control device 32 is provided by a so-called microcomputer including a CPU (central processing unit) 70, a ROM (read only memory) 72, a RAM (random access memory) 74, and an I/O (input-and-output) port, not shown. The CPU 70 processes signals according to the control programs pre-stored in the ROM 72 by utilizing the temporary-storage function of the RAM 74, and supplies drive signals via the I/O port to the air pumps 24, 58 and the pressure control valves 18, 60 so as to control the cuff pressure PC and the pressure in the pressure chamber 56. Moreover, the CPU 70 determines, based on the cuff-pulse-wave signal SM1 supplied from the pulse-wave filter circuit 28, a blood-pressure value BP of the patient, and additionally compares the thus determined blood-pressure value BP and a pressure represented by the carotid pulse wave wc supplied from the pressure-pulse-wave sensor 54, with each other, so as to judge whether a shape or form of the carotid pulse wave wc is accurate or not, i.e., whether a state in which the pressure-pulse-wave sensor 54 is worn is appropriate or not. A result of this judgment is displayed on a display device 76.

Figure 5:
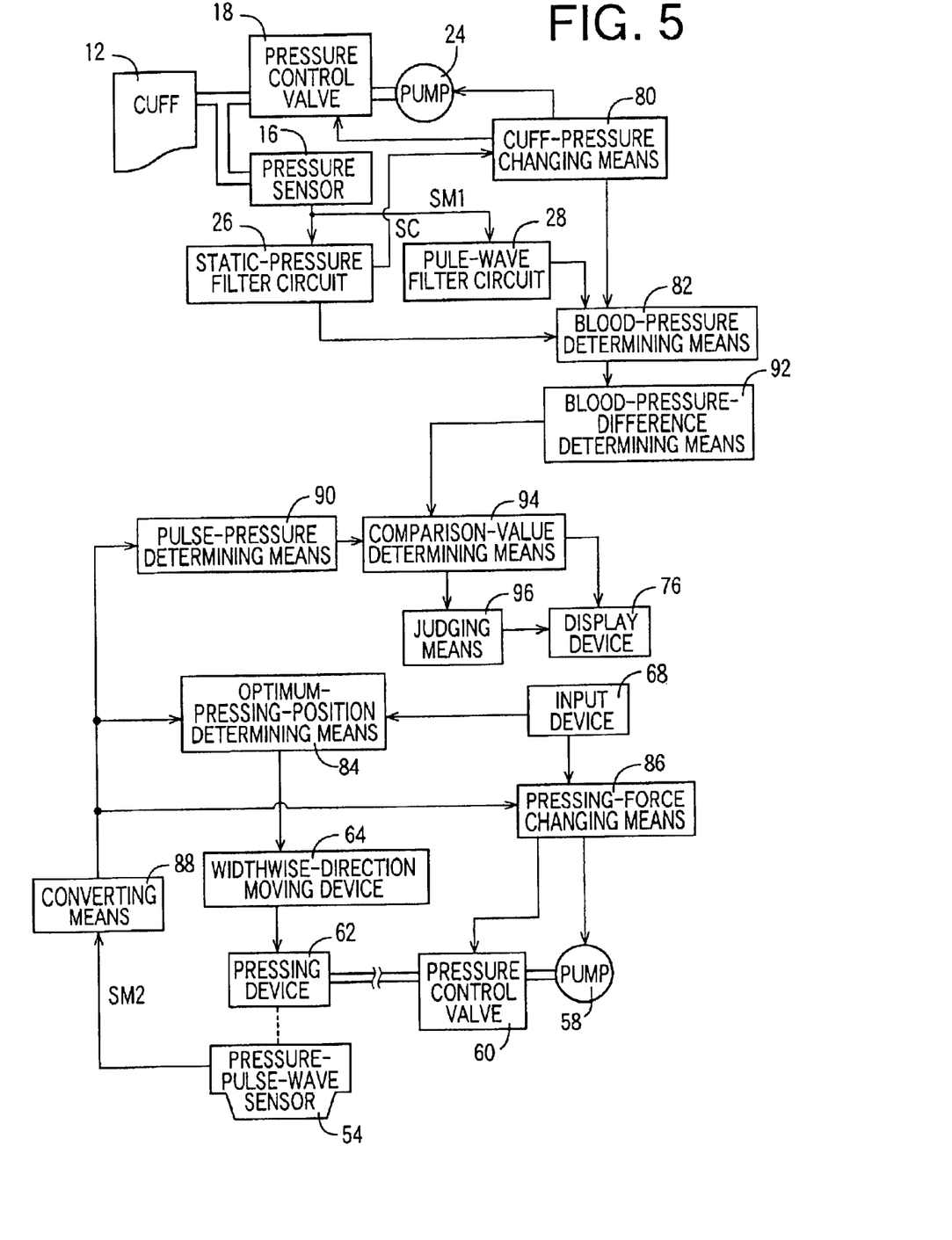
FIG. 5 is a block diagram for explaining essential control functions of an electronic control device of the apparatus of FIG. 1.

FIG. 5 is a block diagram for explaining the essential control functions of the control device 32 of the pressure-pulse-wave detecting apparatus 10. A cuff-pressure changing means 80 operates, based on the cuff-pressure signal SC supplied from the static-pressure filter circuit 26, the pressure control valve 18 and the air pump 24 so as to quickly increase the cuff pressure PC to a prescribed increase-target pressure $PC_M$ (e.g., 180 mmHg) that would be higher than a systolic blood pressure $BP_{SYS}$ of the patient and, subsequently, slowly decrease the cuff pressure at a rate of, e.g., 2 or 3 mmHg/sec. After a blood-pressure determining means 82, described below, determines blood-pressure values BP of the patient, the changing means 80 releases the cuff pressure to an atmospheric pressure.

The blood-pressure determining means 82 determines, based on the cuff-pressure signal SC continuously supplied from the static-pressure filter circuit 26, and the cuff-pulse-wave signal SM1 continuously supplied from the pulse-wave filter circuit 28, each during the slow decreasing of the cuff pressure PC under the control of the cuff-pressure changing means 80, a systolic blood pressure $BP_{SYS}$, a mean blood pressure $BP_{MEAN}$, and a diastolic blood pressure $BP_{DIA}$ of the patient, according to well-known oscillometric method. In the pressure-pulse-wave detecting apparatus 10 shown in FIG. 1, the cuff 12, the pressure sensor 16, the pressure control valve 18, the air pump 24, the static-pressure filter circuit 26, the pulse-wave filter circuit 28, the cuff-pressure changing means 80, and the blood-pressure determining means 82 cooperate with one another to provide a blood-pressure measuring device.

An optimum-pressing-position determining means 84 operates in a manner as described below, when the pressure-pulse-wave sensor 54 is worn on the neck portion, or when the pressing-position changing signal is supplied from the input device 68 to the control device 32.

More specifically described, first, the determining means 84 judges whether a prescribed pressing-position changing condition is satisfied, i.e., whether one (hereinafter, referred to as the "highest-pressure detecting element EM") of the pressure-sensing elements E of the pressure-pulse-wave sensor 54 that detects the highest pressure of the respective pressures detected by all the elements E is positioned in one of prescribed opposite end portions of the array of pressure-sensing elements E. Each of the prescribed opposite end portions of the array of elements E may be a range having a prescribed length including a corresponding one of the opposite ends of the array of elements E, or a range accommodating a prescribed number of elements E including a corresponding one of the respective elements E located at the opposite ends of the array. The highest-pressure detecting element EM is one of the elements E that is positioned right above the carotid artery 46. When this pressing-position changing condition is satisfied, the optimum-pressing-position determining means 84 carries out the following pressing-position changing operation: After the pressing device 62 once moves the pressure-pulse-wave sensor 54 away from the body surface 50, the widthwise-direction moving device 64 moves the pressing device 62 and the sensor 54 over a prescribed distance, and then the pressing device 62 again presses the sensor 54 with a prescribed, considerably low first pressing force HDP1. In this state, the determining means 84 judges again whether the prescribed pressing-position changing condition is satisfied. The determining means 84 repeats carrying out the above-described operation and judgment till the pressing-position changing condition is not satisfied any longer, preferably till the highest-pressure detecting element EM is positioned in a prescribed middle portion of the array of elements E. The length, or element number, employed for each of the opposite end portions of the array of elements E is prescribed based on the diameter of the artery (i.e., the carotid artery 46) to be pressed by the pressure-pulse-wave sensor 54, and may be one fourth of the diameter.

A pressing-force changing means 86 controls the air pump 58 and the pressure control valve 60 so as to change the pressing force HDP at which the pressing device 62 presses the pressure-pulse-wave sensor 54, to the pressing force HDP set by the operator through the input device 68.

A converting means 88 continuously converts, according to a relationship between (a) magnitude of pressure-pulse-wave signal SM2 and (b) pressure, pre-stored in the ROM 72, respective magnitudes or voltages of the pressure-pulse-wave signal SM2 continuously supplied from the pressure-pulse-wave sensor 54, into respective pressure values (mmHg), such that as the signal voltages SM2 increase, the pressure values (mmHg) increase.

A pulse-pressure determining means 90 first determines the highest and lowest pressure values of respective pressure values of one heartbeat-synchronous pulse of the carotid pulse wave wc that have been continuously converted by the converting means 88 from the pressure-pulse-wave signal SM2, and additionally determines a pulse pressure, PP, by subtracting the lowest pressure value from the highest pressure value.

A blood-pressure-difference determining means 92 determines a blood-pressure difference, $\Delta BP$, by subtracting the diastolic blood-pressure value $BP_{DIA}$ determined by the blood-pressure determining means 82, from the systolic blood-pressure value $BP_{SYS}$ determined by the same.

A comparison-value determining means 94 determines a comparison value based on the pulse pressure PP determined by the pulse-pressure determining means 90 and the blood-pressure difference ΔBP determined by the blood-pressure-difference determining means 92, and operates the display device 76 to display the thus determined comparison value. The comparison value determined by the determining means 94 may be any value that indicates a relativity between the pulse pressure PP and the blood-pressure difference ΔBP; for example, a ratio, R, of one of pulse pressure PP and blood-pressure difference ΔBP to the other (R=PP/ΔBP, or ΔBP/PP), a difference, d, of one of pulse pressure PP and blood-pressure difference ΔBP from the other (R=PP−ΔBP, or ΔBP−PP), or a value (=d/R) obtained by dividing difference d by ratio R.

Here, the meaning of the term "comparison value" is explained in more detail. Pulse pressure PP is a difference between the highest and lowest pressure values of one heartbeat-synchronous pulse of carotid pulse wave wc, and blood-pressure difference ΔBP is a difference between systolic and diastolic blood-pressure values. The blood-pressure values determined by the blood-pressure determining means 82 are highly reliable. Thus, if the comparison value is near to a value indicating that pulse pressure PP is equal to blood-pressure difference ΔBP (for example, if the ratio R is near to one), then it can be said that the pressure represented by the shape or form of the carotid pulse wave wc is accurate, and that the pressure-pulse-wave sensor 54 is worn in an appropriate state. On the other hand, if pulse pressure PP is much smaller than blood-pressure difference ΔBP, then it can be concluded that the sensor 54 is worn in an inappropriate state (e.g., worn at an inappropriate position, or pressed with an inappropriate force), and that the form of the pulse wave detected is not accurate. Therefore, an operator such as a doctor or a nurse can judge, based on the comparison value displayed on the display device 76, whether the form of the carotid pulse wave wc is accurate, or whether the pressure-pulse-wave sensor 54 is worn in an appropriate state.

A judging means 96 judges, based on the comparison value determined by the comparison-value determining means 94, whether the pressure-pulse-wave sensor 54 is worn in an appropriate state, and operates the display device 76 to display a result of the judgment. As explained above, if the comparison value is near to the value indicating that pulse pressure PP is equal to blood-pressure difference ΔBP, it can be judged that the pressure-pulse-wave sensor 54 is worn in an appropriate state. For example, if the pressure ratio R as the comparison value is near to one, or if the pressure difference d as the comparison value is near to zero, it can be judged that the pressure-pulse-wave sensor 54 is worn in an appropriate state. Thus, if the comparison value falls within a normal range that is experimentally determined in advance, then the judging means 96 judges that the sensor 54 is worn in an appropriate state. If the ratio R is used as the comparison value, the normal range may be a range including one; and if the difference d is used as the comparison value, the normal range may be a range including zero.

Figure 6:
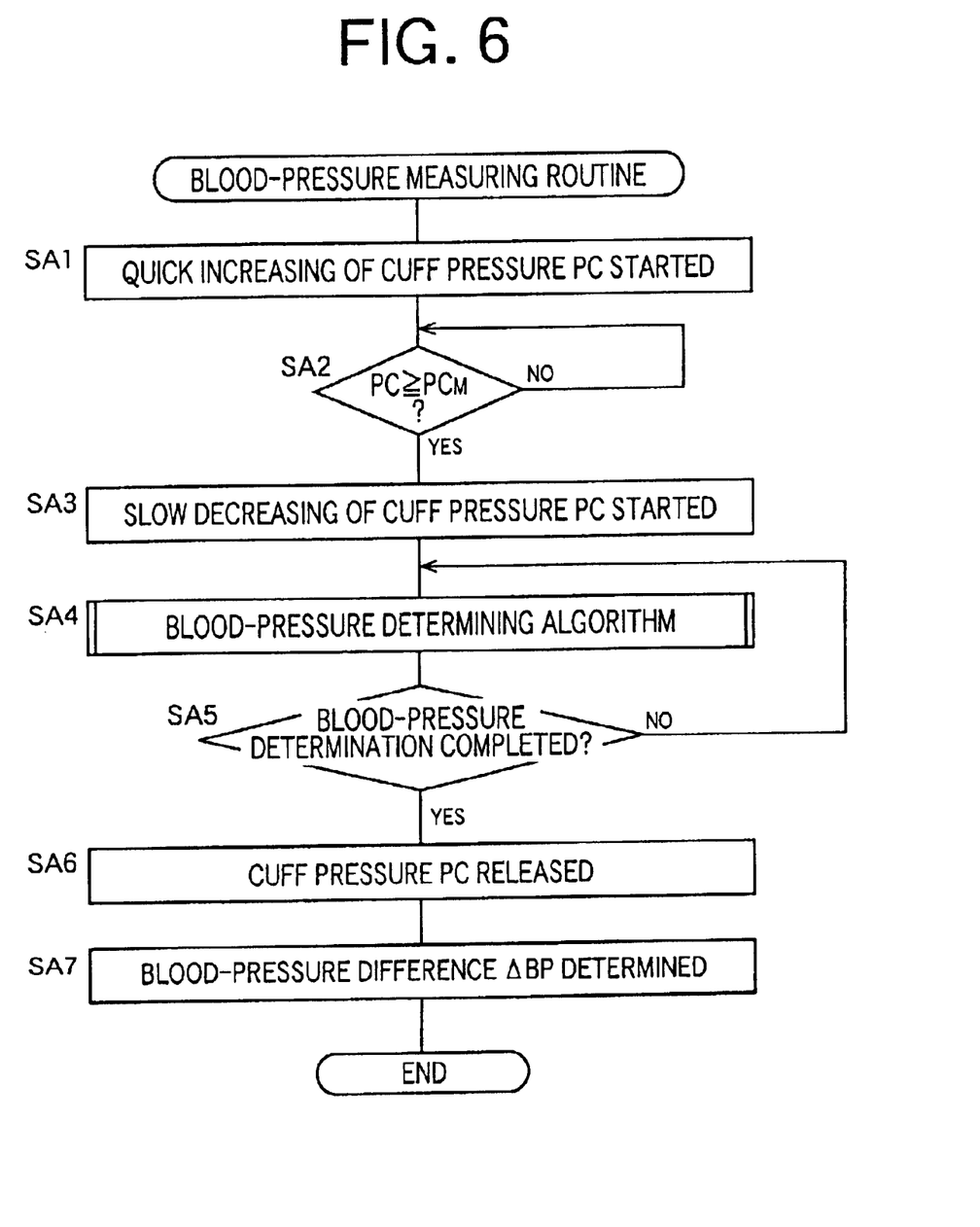
FIG. 6 is a flow chart representing a blood-pressure measuring routine including a portion of the control functions of the control device, shown in FIG. 5.
Figure 7:
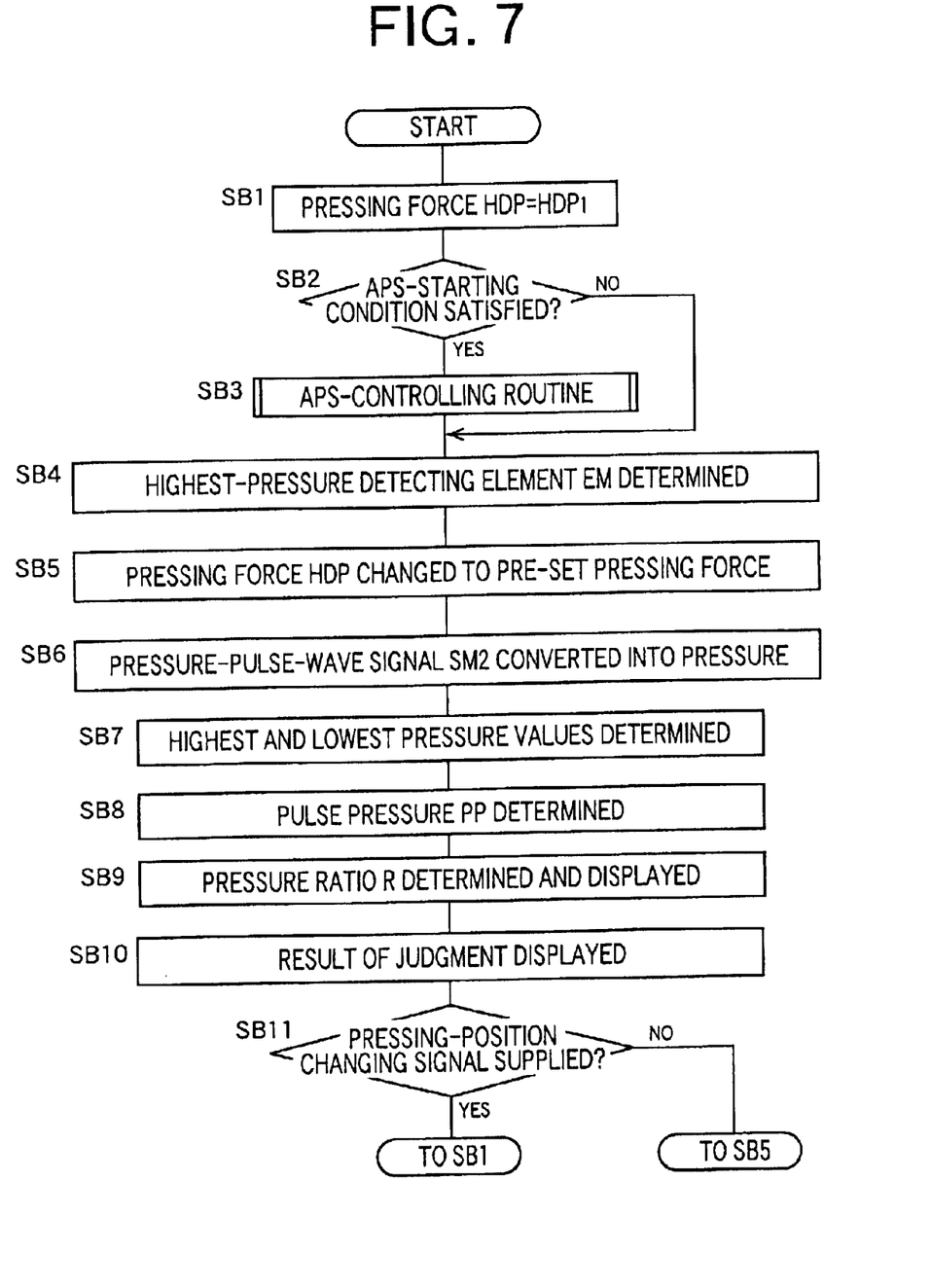
FIG. 7 is a flow chart representing a main routine including the other portions of the control functions of the control device, shown in FIG. 6.

FIGS. 6 and 7 are flow charts representing the control functions of the control device 32, shown in the diagrammatic view of FIG. 5. More specifically described, FIG. 6 shows a blood-pressure measuring routine; and FIG. 7 shows a main routine.

In FIG. 6, first, the control device 32 carries out Step SA1 (hereinafter, terms "Step(s)" are omitted). At SA1, the control device starts the air pump 24 and operates the pressure control valve 18 so as to start quickly increasing the cuff pressure PC. Subsequently, at SA2, the control device judges whether the cuff pressure PC has exceeded an increase-target pressure value $PC_M$ pre-set at 180 mmHg. SA2 is repeated until a positive judgment is made, while the cuff pressure PC is quickly increased. Meanwhile, if a positive judgment is made at SA2, the control goes to SA3 to stop the air pump 24 and operate the pressure control valve 18 so as to start slowly decreasing the cuff pressure PC at a rate of about 3 mmHg/sec.

Next, the control goes to SA4 and SA5 corresponding to the blood-pressure determining means 82. At SA4, the control device determines, based on the change of respective amplitudes of successive heartbeat-synchronous pulses of the brachial pulse wave represented by the cuff-pulse-wave signal SM1 continuously obtained during the slow decreasing of the cuff pressure PC, a systolic blood pressure $BP_{SYS}$, a mean blood pressure $BP_{MEAN}$, and a diastolic blood pressure $BP_{DIA}$ of the subject, according to well-known oscillometric blood-pressure determining algorithm. Then, at SA5, the control device judges whether the determination of the blood-pressure values BP has completed at SA4. Since the diastolic blood pressure $BP_{DIA}$ is last determined at SA4, the control device judges, at SA5, whether the diastolic blood pressure $BP_{DIA}$ has been determined. SA4 is repeated until a positive judgment is made at SA5, while the blood-pressure determining algorithm is continued.

Meanwhile, if a positive judgment is made at SA5, the control goes to SA6 to operate the pressure control valve 18 to decrease the cuff pressure PC to an atmospheric pressure. In the flow chart of FIG. 6, SA1 to SA3 and SA6 correspond to the cuff-pressure changing means 80.

Next, the control goes to SA7 corresponding to the blood-pressure-difference determining means 92. At SA7, the control device determines a blood-pressure difference ΔBP by subtracting the diastolic blood pressure $BP_{DIA}$ determined at SA4, from the systolic blood pressure $BP_{SYS}$ determined there.

Then, the control device carries out the main routine shown in FIG. 7. It is preferred, but is not essentially required, that the main routine be carried out immediately after the blood-pressure measuring routine shown in FIG. 6.

First, the control device carries out SB1 to SB3 corresponding to the optimum-pressing-position determining means 84. At SB1, the control device operates the pressure control valve 60 and the air pump 58 to change the pressure in the pressure chamber 56 and thereby change the pressing force HDP applied to the pressure-pulse-wave sensor 54, to a pre-set first pressing force HDP1. This first pressing force HDP1 is experimentally determined, in advance, as a pressing force HDP that assures that respective S/N ratios of respective carotid pulse waves wc detected by the respective pressure-sensing elements E are so great as to be able to determine respective magnitudes of respective peak points of those carotid pulse waves wc.

Then, at SB2, the control device judges whether a pressing-position updating condition (i.e., an APS starting condition) has been satisfied, e.g., whether the highest-pressure detecting element EM out of the pressure-sensing elements E provided in the press surface 66 of the pressure-pulse-wave sensor 54 is located in one of prescribed opposite end portions of the array of elements E. If a negative judgment is made at SB2, the control goes to SB4 and the following steps, described later.

On the other hand, if a positive judgment is made at SB2, i.e., if a current position of the pressure-pulse-wave sensor 54 relative to the carotid artery 46 is not appropriate, the control goes to SB3 to perform an APS-controlling routine. In this routine, the control device operates for moving the sensor 54 to an optimum pressing position where the highest-pressure detecting element EM is located at substantially the middle of the array of elements E. More specifically, first, the control device operates the pressing device 62 to once move the sensor 54 off the body surface 50, subsequently operates the widthwise-direction moving device 64 to move the pressing device 62 and the sensor 54 over a predetermined distance, and then operates the pressing device 62 to press again the sensor 54 at the first pressing force HDP1. In this state, the control device judges whether the highest-pressure detecting element EM is located in a prescribed middle range of the array of pressure-sensing elements E. The above-described pressing and judging operations are repeated until a positive judgment is made.

If at SB3 the pressure-pulse-wave sensor 54 is positioned at the optimum pressing position, or if a negative judgment is made at SB2, the control goes to SB4 to identify the highest-pressure detecting element EM in the current condition.

Then, the control goes to SB5 corresponding to the pressing-force changing means 86. At SB5, the control device operates the pressure control valve 60 so that the pressing force HDP applied by the pressing device 62 to the sensor 54 is changed to the pre-set pressing force represented by the pressing-force signal supplied from the input device 68. If no pressing-force signal is supplied from the input device 68, then a default value is used in place of the pre-set pressing force.

Then, the control goes to SB6 corresponding to the converting means 88. At SB6, the control device converts, according to the signal-pressure relationship pre-stored in the ROM 72, respective magnitudes of respective points of the pressure-pulse-wave signal SM2 continuously supplied from the pressure-pulse-wave sensor 54, into pressure values (mmHg).

Subsequently, the control goes to SB7 and SB8 corresponding to the pulse-pressure determining means 90. At SB7, the control device stores the pressure values that have been converted, at SB6, from a length of the pressure-pulse-wave signal SM2 that corresponds to one heartbeat-synchronous pulse of the carotid pulse wave wc. In addition, the control device determines the highest and lowest pressure values of the thus stored pressure values. Then, at SB8, the control device determines a pulse pressure PP by subtracting the lowest pressure determined at SB7, from the highest pressure determined at the same step.

Then, the control goes to SB9 corresponding to the comparison-value determining means 94. At SB9, the control device divides the pulse pressure PP determined at SB8, by the blood-pressure difference ΔBP determined at SB7 of FIG. 6, thereby determining a pressure ratio R as the comparison value. In addition, the control device operates the display device 76 to display the thus determined pressure ratio R.

Subsequently, the control goes to SB10 corresponding to the judging means 96. At SB10, the control device judges whether the pressure ratio R determined at SB9 falls within a pre-set normal range that is not smaller than 0.8. If a positive judgment is made, the control device judges that the pressure-pulse-wave sensor 54 is worn in an appropriate state, and operates the display device 76 to display characters or symbols that indicates the positive judgment. On the other hand, if a negative judgment is made, the control device judges that the pressure-pulse-wave sensor 54 is worn in an inappropriate state, and operates the display device 76 to display characters or symbols that indicates the negative judgment.

From the pressure ratio R, and the result of judgment about the state in which the pressure-pulse-wave sensor 54 is worn, both displayed on the display device 76 at SB9 and SB10, the operator of the present apparatus 10 can know about whether the state in which the sensor 54 is worn is appropriate or not. The position where the sensor 54 is worn is appropriate immediate after a negative judgment is made at SB2 or immediately after SB3 is carried out. However, the position where the sensor 54 is worn may be changed by, e.g., a physical motion of the patient or the like. In this case, the operator may operate the input device 68 to change the current position where the sensor 54 is worn. Thus, the pressing-position changing signal may be supplied from the input device 68 to the control device. Hence, at SB11, the control device judges whether it has received the pressing-position changing signal from the input device 68. If a positive judgment is made at SB11, the control goes back to SB1 and the following steps, so as to change the position where the sensor 54 is worn.

Immediately after the APS-controlling routine is carried out at SB3, the position where the pressure-pulse-wave sensor 54 is worn should be appropriate. If, nonetheless, the display device 76 displays the characters or symbols indicating that the state in which the sensor 54 is worn is not appropriate, then the operator can judge that the pressing force HDP applied to the sensor 54 may not be appropriate. In this case, the operator may operate the input device 68 to set a new pressing force and supply a pressing-force signal representing the thus set new pressing force, to the control device, so as to change the current pressing force. On the other hand, from what is displayed on the display device 76, the operator may judge that the state in which the sensor 54 is worn is appropriate. Therefore, if a negative judgment is made at SB11, the control goes back to SB5 and the following steps. Thus, the detection of the carotid pulse wave wc is continued either while the position where the sensor 54 is worn is not changed and only the pressing force HDP is changed, or while neither the position nor the pressing force HDP is changed.

While the main routine shown in FIG. 7 is repeatedly carried out, the operator will eventually be able to judge that the state in which the pressure-pulse-wave sensor 54 is worn is appropriate and that the form of the carotid pulse wave wc detected by the sensor 54 is accurate. Then, the carotid pulse wave wc can be used to measure an accurate pulse-wave propagation velocity PWV of the patient, or determine an accurate augmentation index AI of the patient.

In the embodiment employing the above-described flow charts, the control device 32 determines, at SA4 and SA5 (the blood-pressure determining means 82), the blood-pressure values BP that can be said as accurate intraarterial pressure values. Therefore, if the pressure ratio R determined at SB9 (the comparison-value determining means 94) is near to one, it can be judged that the pressure values represented by the pressure-pulse-wave signal SM2 (i.e., the carotid pulse wave wc) accurately indicate the intraarterial pressure values. In this case, it can also be judged that there is no attenuation of the pressure pulse wave because of the artery's wall and/or the skin or subcutaneous tissue, and that the form of the carotid pulse wave wc is accurate.

In addition, in the embodiment employing the above-described flow charts, the control device judges, at SB10

(the judging means 96), whether the state in which the pressure-pulse-wave sensor 54 is worn is appropriate, based on the pressure ratio R determined at SB9 (the comparison-value determining means 96), and operates the display device 76 to display the result of judgment. Therefore, the operator can easily know about whether the state in which the pressure- pulse-wave sensor 54 is worn is appropriate.

While the present invention has been described in its preferred embodiment by reference to the drawings, it is to be understood that the invention may otherwise be embodied.

For example, in the illustrated apparatus 10, the pressure-pulse-wave sensor 54 is adapted to be worn on the neck portion 38 of the patient. However, it is possible to employ a pressure-pulse-wave sensor of a different type that is adapted to be worn on a different portion, such as an upper arm, a wrist, or a femoral portion.

In the illustrated pressure-pulse-wave detecting apparatus 10, the relationship between pressure-pulse-wave signal SM2 and pressure (mmHg) is pre-determined, and is pre-stored in the ROM 72. However, the control device 32 may be one which can determine a relationship between pressure-pulse-wave signal SM2 and pressure (mmHg), based on a fact that the highest and lowest pressure values of the respective pressure values corresponding to one heartbeat-synchronous pulse of the pressure pulse wave detected by the pressure-pulse-wave sensor 54, correspond to the systolic and diastolic blood-pressure values $BP_{SYS}$, $BP_{DIA}$ determined by the blood-pressure determining means 82, respectively.

In the illustrated pressure-pulse-wave detecting apparatus 10, the display device 76 displays the result of judgment about whether the state in which the pressure-pulse-wave sensor 54 is worn is appropriate. However, the apparatus 10 may be one which automatically changes, based on the result of judgment, the state in which the sensor 54 is worn.

The pressing device 62 employed in the illustrated apparatus 10 can press the pressure-pulse-wave sensor 54 with a changeable pressing force. However, the pressing device 62 may be one which presses the sensor 54 with a pre-set pressing force.

The blood-pressure measuring device employed in the illustrated apparatus 10 measures blood-pressure values according to so-called oscillometric method. However, the oscillometric blood-pressure measuring device may be replaced with so-called Korotkoff-sound blood-pressure measuring device which determines, as blood-pressure values, respective cuff-pressure values at the respective times of detection of the first and last Korotkoff sounds. Otherwise, it is possible to employ a supersonic-Doppler-type blood-pressure measuring device which includes supersonic-wave generator and detector that are adapted to be placed right above an artery, and which detects, using the generator and the detector, opening and closing of the artery when a pressing force applied to the artery is changed.

The comparison-value determining means 94 shown in FIG. 5 determines the comparison value based on the pulse pressure PP of the carotid pulse wave wc and the blood-pressure value ΔBP. However, the greatest value (i.e., the peak value), area-gravity-center value, and smallest value of one heartbeat-synchronous pulse of the carotid pulse wave wc correspond to the systolic blood-pressure value $BP_{SYS}$, mean blood-pressure value $BP_{MEAN}$, and diastolic blood-pressure value $BP_{DIA}$ of the patient, respectively. Therefore, the comparison-value determining means 94 may be so modified as to determine a comparison value based on a difference between the greatest value and the area-gravity-center value of the carotid pulse wave wc and a difference between the systolic blood-pressure value $BP_{SYS}$ and the mean blood-pressure value $BP_{MEAN}$, or based on a difference between the area-gravity-center value and the smallest value of one heartbeat-synchronous pulse of the carotid pulse wave wc and a difference between the mean blood-pressure value $BP_{MEAN}$ and the diastolic blood-pressure value $BP_{DIA}$. Otherwise, the comparison-value determining means 94 may be so modified as to determine a comparison value based on the greatest value of the carotid pulse wave wc and the systolic blood-pressure value $BP_{SYS}$, based on the area-gravity-center value of the pulse wave wc and the mean blood-pressure value $BP_{MEAN}$, or based on the smallest value of the pulse wave wc and the diastolic blood-pressure value $BP_{DIA}$.

The present invention may be embodied with other various changes without departing from the spirit of the invention.

What is claimed is:

1. An apparatus for detecting a pressure pulse wave from a living subject, comprising:

a pressure-pulse-wave sensor which is adapted to be pressed against a portion of the subject to detect the pressure pulse wave from the subject;

a pressing device which presses the pressure-pulse-wave sensor against the portion of the subject;

a blood-pressure measuring device which measures at least one blood pressure value of the subject; and a comparison-value determining means for determining a comparison value based on said at least one blood pressure value measured by the blood-pressure measuring device and at least one pressure value corresponding to the pressure pulse wave detected by the pressure-pulse-wave sensor, wherein the blood-pressure measuring device measures a systolic blood pressure value and a diastolic blood pressure value of the subject, and wherein the comparison-value determining means determines the comparison value based on a difference between the systolic and diastolic blood pressure values measured by the blood-pressure measuring device and a pulse pressure corresponding to the pressure pulse wave detected by the pressure-pulse-wave sensor.

2. An apparatus according to claim 1, further comprising a judging means for judging, based on the comparison value determined by the comparison-value determining means, whether a state in which the pressure-pulse-wave sensor is worn on the portion of the subject is appropriate.

3. An apparatus according to claim 2, wherein the judging means judges whether the comparison value determined by the comparison-value determining means falls within a prescribed normal range, and judges, if a positive judgment is made, that the state in which the pressure-pulse-wave sensor is worn is appropriate and, judges if a negative judgment is made, that the state is not appropriate.

4. An apparatus according to claim 1, wherein the comparison-value determining means comprises a blood-pressure-difference determining means for determining the difference between the systolic and diastolic blood pressure values measured by the blood-pressure measuring device, and a pulse-pressure determining means for determining the pulse pressure as a difference between a highest pressure and a lowest pressure of pressure values corresponding to one heartbeat-synchronous pulse of the pressure pulse wave detected by the pressure-pulse-wave sensor.

5. An apparatus according to claim 4, wherein the pressure-pulse-wave sensor produces an electric signal representing the pressure pulse wave detected thereby, and wherein the comparison-value determining means further comprises a converting means for converting respective voltages of respective points of the electric signal produced by the pressure-pulse-wave sensor, into respective pressure values, according to a prescribed relationship between voltage and pressure.

6. An apparatus according to claim 5, wherein the comparison-value determining means further comprises a memory which stores the prescribed relationship between voltage and pressure.

7. An apparatus according to claim 1, wherein the comparison-value determining means determines, as the comparison value, a value obtained by dividing the pulse pressure corresponding to the pressure pulse wave detected by the pressure-pulse-wave sensor, by the difference between the systolic and diastolic blood pressure values measured by the blood-pressure measuring device.

8. An apparatus according to claim 1, further comprising an input device which is operable to input a desired pressing force and supply a pressing-force signal representing the inputted pressing force, to the pressing device, so that the pressing device presses the pressure-pulse-wave sensor with the inputted pressing force.

9. An apparatus according to claim 1, further comprising:

a moving device which moves the pressure-pulse-wave sensor in a direction crossing an artery of the portion of the subject; and an input device which is operable to input a pressing-position changing command and supply a pressing-position changing signal representing the inputted pressing-position changing command, to the moving device, so that the moving device moves the pressure-pulse-wave sensor in the direction crossing the artery.

10. An apparatus for detecting a pressure pulse wave from a living subject, comprising:

a pressure-pulse-wave sensor which is adapted to be pressed against a portion of the subject to detect the pressure pulse wave from the subject;

a pressing device which presses the pressure-pulse-wave sensor against the portion of the subject;

a blood-pressure measuring device which measures at least one blood pressure value of the subject; and a comparison-value determining means for determining a comparison value based on said at least one blood pressure value measured by the blood-pressure measuring device and at least one pressure value corresponding to the pressure pulse wave detected by the pressure-pulse-wave sensor;

a judging means for judging, based on the comparison value determined by the comparison-value determining means, whether a state in which the pressure-pulse-wave sensor is worn on the portion of the subject is appropriate; and a display device which displays a result of judgment made by the judging means.

11. An apparatus for detecting a pressure pulse wave from a living subject, comprising:

a pressure-pulse-wave sensor which is adapted to be pressed against a portion of the subject to detect the pressure pulse wave from the subject;

a pressing device which presses the pressure-pulse-wave sensor against the portion of the subject;

a blood-pressure measuring device which measures at least one blood pressure value of the subject; and a comparison-value determining means for determining a comparison value based on said at least one blood pressure value measured by the blood-pressure measuring device and at least one pressure value corresponding to the pressure pulse wave detected by the pressure-pulse-wave sensor; and a display device which displays the comparison value determined by the comparison-value determining means.

* * * * *